(12) United States Patent
Smith, III et al.

(10) Patent No.: US 6,450,936 B1
(45) Date of Patent: Sep. 17, 2002

(54) MANIFOLD DEVICE FOR MANIPULATION OF RADIOACTIVE FLUID

(75) Inventors: Edward F. Smith, III, Las Flores, CA (US); David W. Pipes, Chesterfield, MO (US); James G. Schnieder, Chesterfield, MO (US)

(73) Assignee: Mallinckrodt Inc., St. Louis, MO (US)

( * ) Notice: Subject to any disclaimer, the term of this patent is extended or adjusted under 35 U.S.C. 154(b) by 0 days.

(21) Appl. No.: 09/560,024

(22) Filed: Apr. 27, 2000

Related U.S. Application Data (60) Provisional application No. 60/131,957, filed on Apr. 3, 1999.

(51) Int. Cl.$^7$ .................................................. A61N 5/00
(52) U.S. Cl. ........................................ 600/4; 604/99.01
(58) Field of Search ............................... 600/1, 3, 4, 5; 250/428; 604/98.01, 99.01, 93.01

Primary Examiner—Edward K. Look
Assistant Examiner—Dwayne J. White
(74) Attorney, Agent, or Firm—Jeffrey S. Boone

(57) ABSTRACT

A manifold system allows for the movement of a radioactive fluid from a container to a treatment balloon or other device, and the withdrawal of the radioactive fluid from the treatment device. The system allows for the convenient movement of the fluid, with minimal radiation exposure for those using the system. The manifold system is particularly useful in the use of radiation to prevent restenosis of arteries.

27 Claims, 7 Drawing Sheets

MANIFOLD DEVICE FOR MANIPULATION OF RADIOACTIVE FLUID

This Application claims benefit of Prov. No. 60/131,957 filed Apr. 3, 1999.

BACKGROUND OF THE INVENTION

This invention relates to an apparatus and method for manipulation of a radioactive fluid. This invention also relates to a method of treating stenosis (blocked arteries) and preventing restenosis (re-blocking of the artery) which employs a radioactive fluid.

It is often desired to safely manipulate a radioactive fluid. For instance in oncology, it may be necessary to introduce a radioactive fluid into the body of a patient in for diagnostic or therapeutic purposes. Specifically, a radioactive fluid might be injected into the bloodstream or into a tumor. Alternatively, a radioactive fluid might be introduced into a balloon catheter in order to irradiate tumor cells or other cells.

Percutaneous transluminal angioplasty (PTA) is the general technique of dilatation of a blocked artery (both peripheral and coronary (PTCA) arteries) with mechanical means at the end of a catheter. The use of a balloon catheter in PTA is well known. The catheter is positioned with the balloon at the site of the blockage, typically with the assistance of a guide wire and a fluoroscope, and the balloon inflated at high pressure (e.g.: 6 to 20 atmospheres (0.6 to 2 MPa).

While the use of a balloon catheter in PTA is an effective technique, it is common for the affected artery to become re-blocked in a period of several (typically 3–6) months ("restenosis"). Restenosis is believed to occur as a result of injury to the arterial wall during the PTA procedure. One approach to treating restenosis is to repeat the PTA procedure. However, the expense of PTA and the inconvenience to the patient make this undesirable. An attempt at preventing restenosis is the use of a stent, which is a small, typically metal device that holds the artery open. Stents, however, are only partially effective in preventing restenosis.

An approach that appears to be quite promising is the use of radiation to prevent restenosis. In doses of 8 to 30 Gy, radiation has been shown to be relatively safe and effective in preventing restenosis. While the exact mechanism of action is not known, it is suspected that the radiation "stuns" the cells that cause restenosis, rendering them less able to re-block the artery.

Several approaches have been taken to supplying radiation to the affected site. One is the use of a solid radioactive source (such a beads) fixed in the end of a catheter. After PTA, the PTA catheter would be removed and the radioactive catheter inserted. This technique suffers from the disadvantage of making it difficult to center the radioactive source in the artery so that the artery is uniformly irradiated. Another disadvantage is that the catheter is radioactive the entire time it is in use, causing exposure issues for the patient and the medical personnel.

Another approach is to position a guide wire past the obstruction, slide a balloon catheter over the guide wire to the obstruction, inflate the balloon to perform the angioplasty, remove the guide wire, and replace it with a wire having a radioactive tip. This approach also suffers the disadvantages of difficulties centering the radiation source and the fact that the treatment wire is radioactive during the entire time it is in use, as well as problems associated with removing the guide wire, which may complicate response to a sudden collapse of the artery.

A technique that results in uniform irradiation is the use of a balloon catheter filled with a radioactive fluid, generally a liquid. This method has the advantage of ease of use, including automatic centering of the radiation. Further, since the catheter is not radioactive until after it is inserted into the patient, there is far less undesired radiation exposure for the patient and the medical personnel.

U.S. Pat. No. 5,199,939 (Dake) teaches a general method of preventing restenosis by supplying a source of radiation at the end of a catheter to the affected vessel. Dake uses radioactive pellets at the end of a catheter having variable stiffness along its length.

U.S. Pat. No. 5,195,962 (Martin; Vas-Cath Incorporated) describes a catheter with 3 non-concentric lumens, and a method of manufacturing such a catheter. The central lumen of the catheter can be used for a guide wire. This reference discloses several other multi-lumen catheters.

U.S. Pat. No. 5,207,648 (Gross; The Kendall Company) describes a catheter with 3 concentric lumens.

U.S. Pat. No. 5,226,889 (Sheiban) discloses a catheter having 2 balloons where the distal balloon is used to open an artery and the second, of larger diameter, is used to implant a stent.

U.S. Pat. No. 5,314,409 (Sarosiek; UVA Patents Foundation) teaches an esophageal perfusion catheter having two balloons and multiple lumens. Some of the lumens communicate with ports between the balloons.

U.S. Pat. No. 5,342,306 (Michael) is representative of several disclosures that show two balloons used to isolate a treatment area in an artery so that liquid can be introduced into the space between the balloons without being washed away by blood flow.

WO 96/17654 (Thornton; Omnitron International) teaches the use of a balloon catheter filled with a radioactive liquid. In one embodiment Thornton uses multiple concentric balloons to guard against leakage, etc. In another embodiment Thornton uses a main balloon and two additional balloons on either side of the main balloon to block the flow in the artery in case of rupture of the main balloon, thus preventing flow of radioactive liquid throughout the patient's body.

WO 97/48452 (Lavie; The State of Israel, SOREQ) teaches a device for preventing restenosis with beta radiation from a Rhenium-186 or Rhenium-188. This reference employs several embodiments that place the radiation at the end of a catheter.

WO 98/46309 (Pipes; Mallinckrodt) teaches a double serial balloon in which one balloon is used to perform angioplasty and a second balloon on the same catheter is used to perform the radiation treatment.

SUMMARY OF THE INVENTION

Briefly, the invention comprises a manifold system for manipulating a radioactive fluid. The apparatus and method are particularly suitable for use with a balloon catheter and a radioactive liquid to prevent restenosis. The manifold system provides a convenient and relatively safe method of handling the radioactive fluid. The invention also comprises a method of sequentially removing a radioactive fluid from a container and introducing it into a catheter or other apparatus. The apparatus and method allow for the quick, convenient, and relatively safe radiation treatment of stenosed arteries without the drawbacks associated with many other techniques. The apparatus of the invention can also be used for other situations involving the handling of a radioactive liquid, such as the use of a balloon catheter filled with a radioactive liquid for use in tumor therapy.

DETAILED DESCRIPTION OF THE INVENTION

In this specification and claims, numerical values and ranges are not critical unless otherwise stated. That is, the numerical values and ranges may be read as if they were prefaced with the word "about" or "substantially".

Figure 1:
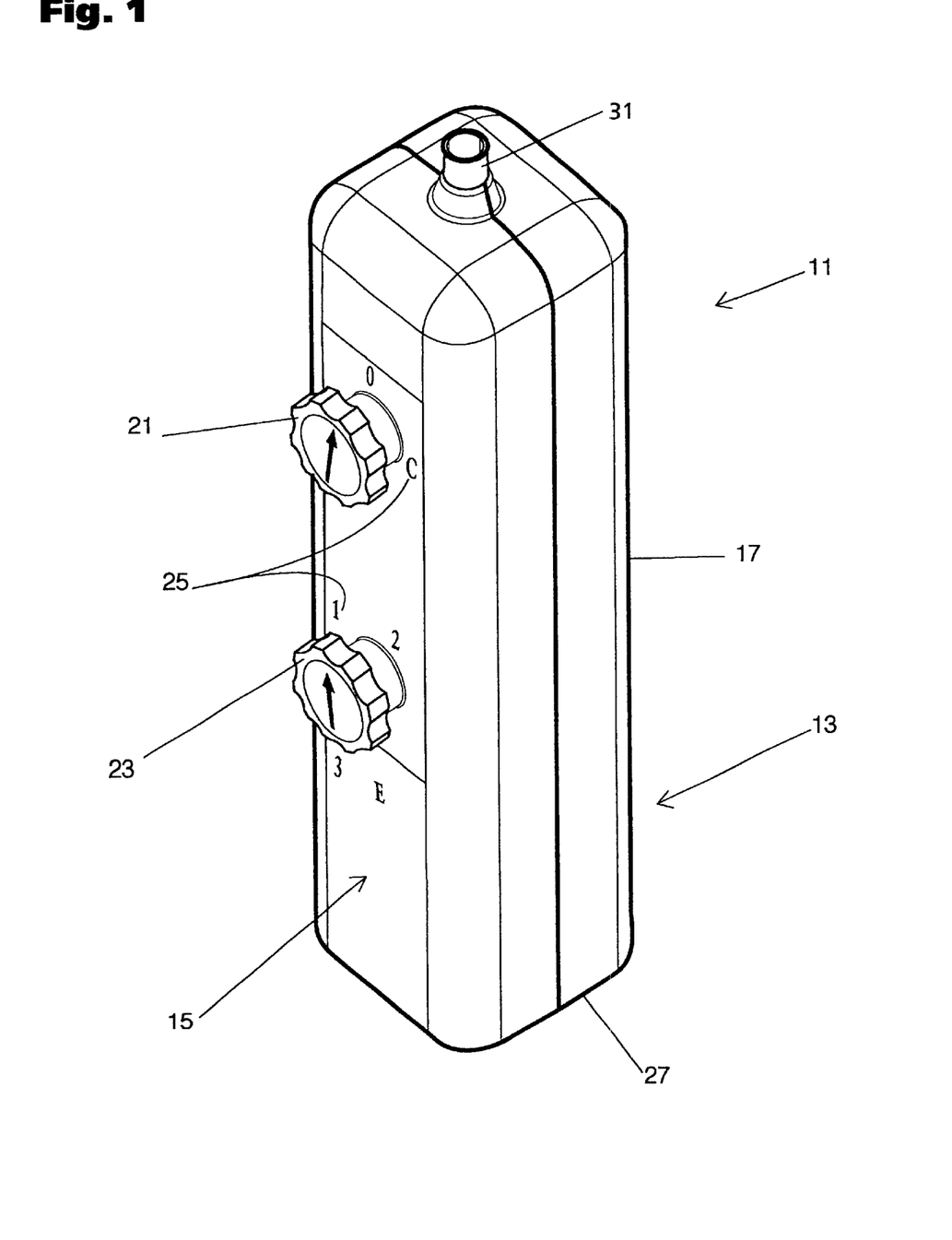
FIG. 1 is a perspective view of a manifold assembly.

Referring first to FIG. 1, a manifold assembly 11 has a housing 13 having a front portion 15 and a rear portion 17. Extending through the face of the front portion 15 are pressure knob 21 and fluid knob 23. Surrounding inlet knob 21 and fluid knob 23 are indica 25 to inform the user of the relative position of the knobs. When in an upright position, manifold assembly 11 rests on its bottom surface 27.

At the top of manifold assembly 11 is a pressure port 31, which is illustratively a luer connection of the type commonly found on medical equipment such as syringes.

Figure 2:
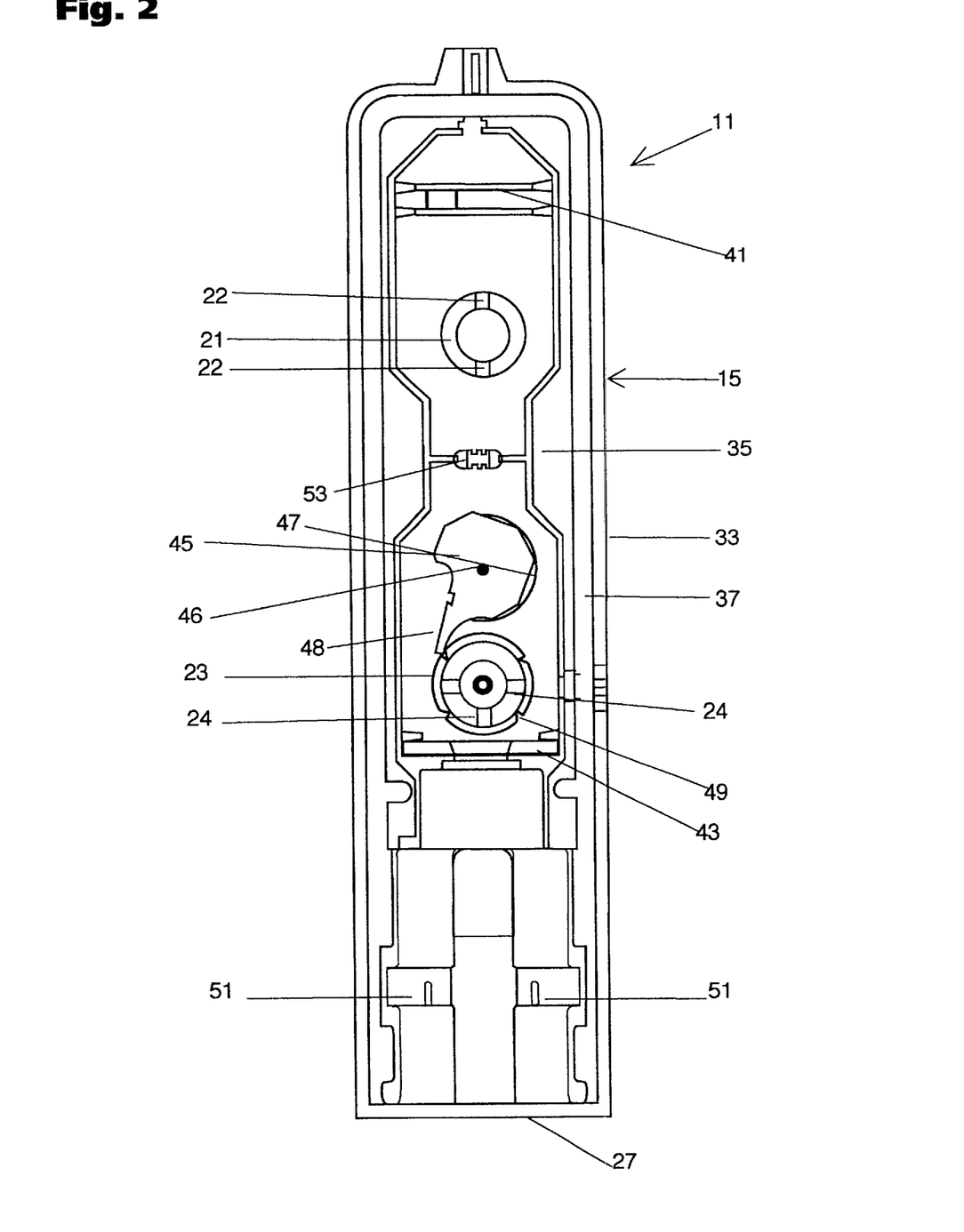
FIG. 2 is a is a view of the front half of the manifold assembly of FIG. 1.

In FIG. 2, the inside of front portion 15 of manifold assembly 11 is shown. The major parts of front portion 15 include an outer shell 33, and inner shell 35 and a lead shield 37 which fits between outer shell 33 and inner shell 35. Additional lead shielding is present at top shield 41 and bottom shield 43.

Also visible inside front portion 15 are the insides of pressure knob 21 and fluid knob 23. The inside face of pressure knob 21 has groves 22 and the inside face of fluid knob 23 has groves 24, which correspond to valve handles (described below). Ratchet 45 pivots on a central pin 46 and is rotated by spring 47 so that pawl 48 engages gaps 49 spaced along the outer periphery of fluid knob 23, permitting fluid knob 23 to be rotated in only one direction (clockwise, as viewed from the perspective of FIG. 1.).

The bottom surface 27 of front portion 15 is open to receive a vial seated in a container shield (both described below). Pins 51 engage gaps on the container shield to retain it in place (described below). Grommet 53 is attached to inner shell 35.

Figure 3:
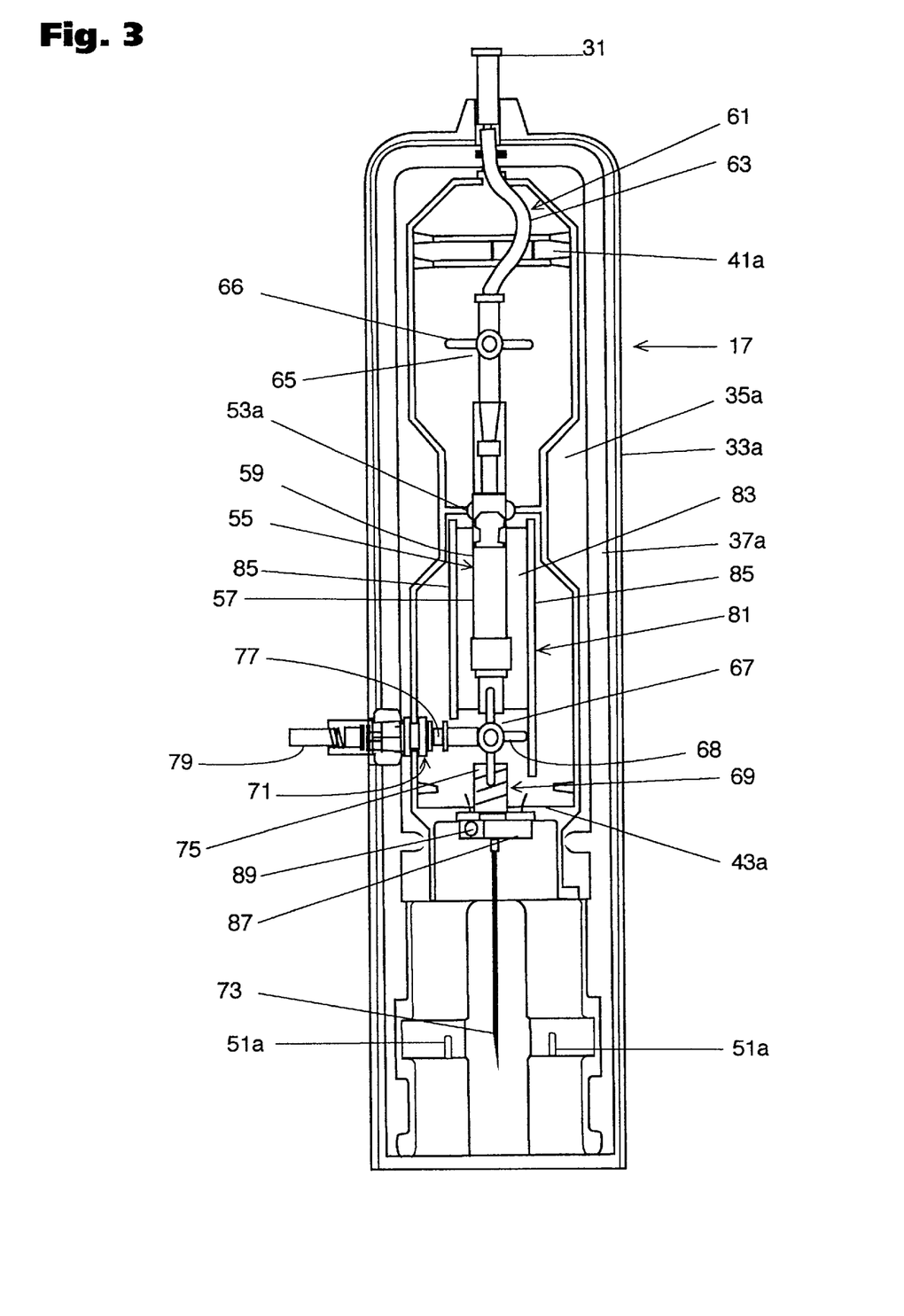
FIG. 3 is a is a view of the back half of the manifold assembly of FIG. 1.

Referring now to FIG. 3, rear portion 17 of manifold assembly 11 is shown. The major parts of rear portion 17 include an outer shell 33a, and inner shell 35a and a lead shield 37a which fits between outer shell 33a and inner shell 35a. Additional lead shielding is present at top shield 41a and bottom shield 43a. Pins 51a are identical to those shown in FIG. 2.

A manifold 55 has a manifold tube 57 having a circular cross section. A plug 59 is slidably received in the interior of tube 57. Manifold tube 57 rests in an inner shield 81 made from a plastic block 83 and lead strips 85. A half grommet 53a, along with half grommet 53 (FIG. 2) supports manifold tube 57.

A pressure path 61 is defined by a pressure tube 63 which terminates at pressure port 31. Pressure tube 63 is curved and passes through an opening defined by top shields 41 and 41a in order to limit the amount of radiation that is able to exit near the top of manifold assembly 11. Pressure valve 65 connects the upper end of manifold tube 57 to pressure tube 63. Pressure valve 65 has a handle 66 which mates with groves 22 of pressure knob 21 (FIG. 2).

A fluid valve 67 has a handle 68 which mates with groves 24 of fluid knob 23. Fluid valve 67 connects the lower end of manifold tube 57 to inlet path 69 and outlet path 71.

Inlet path 69, as illustrated, is a direct connection of hollow needle 73 by means of a luer connection 75. A binding ring 87, tightened by a screw 89, prevents needle 73 from being pushed vertically upward into housing 13. Outlet path 71 is an outlet tube 77 that allows fluid valve 67 to communicate with outlet port 79.

Figure 4:
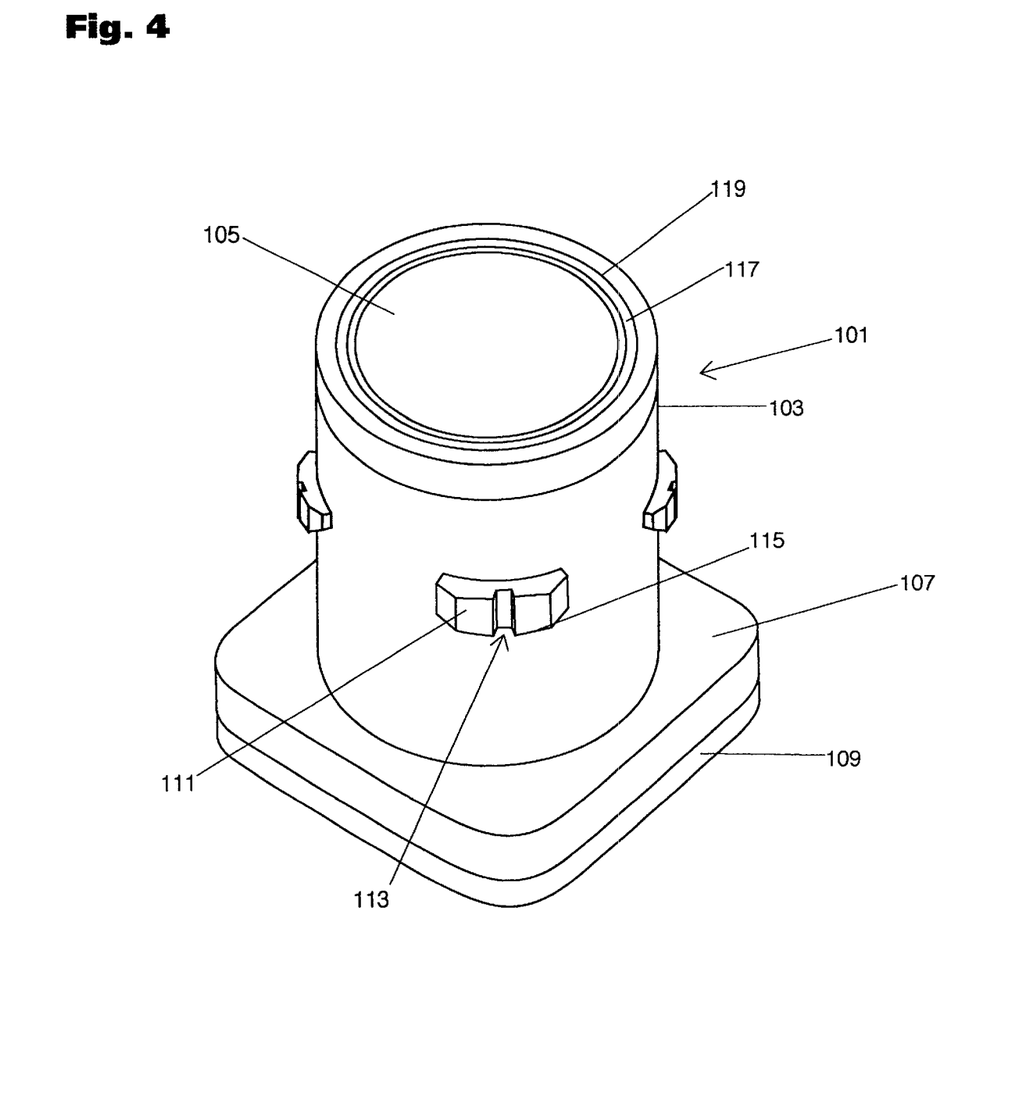
FIG. 4 is a perspective view of a container shield.
Figure 5:
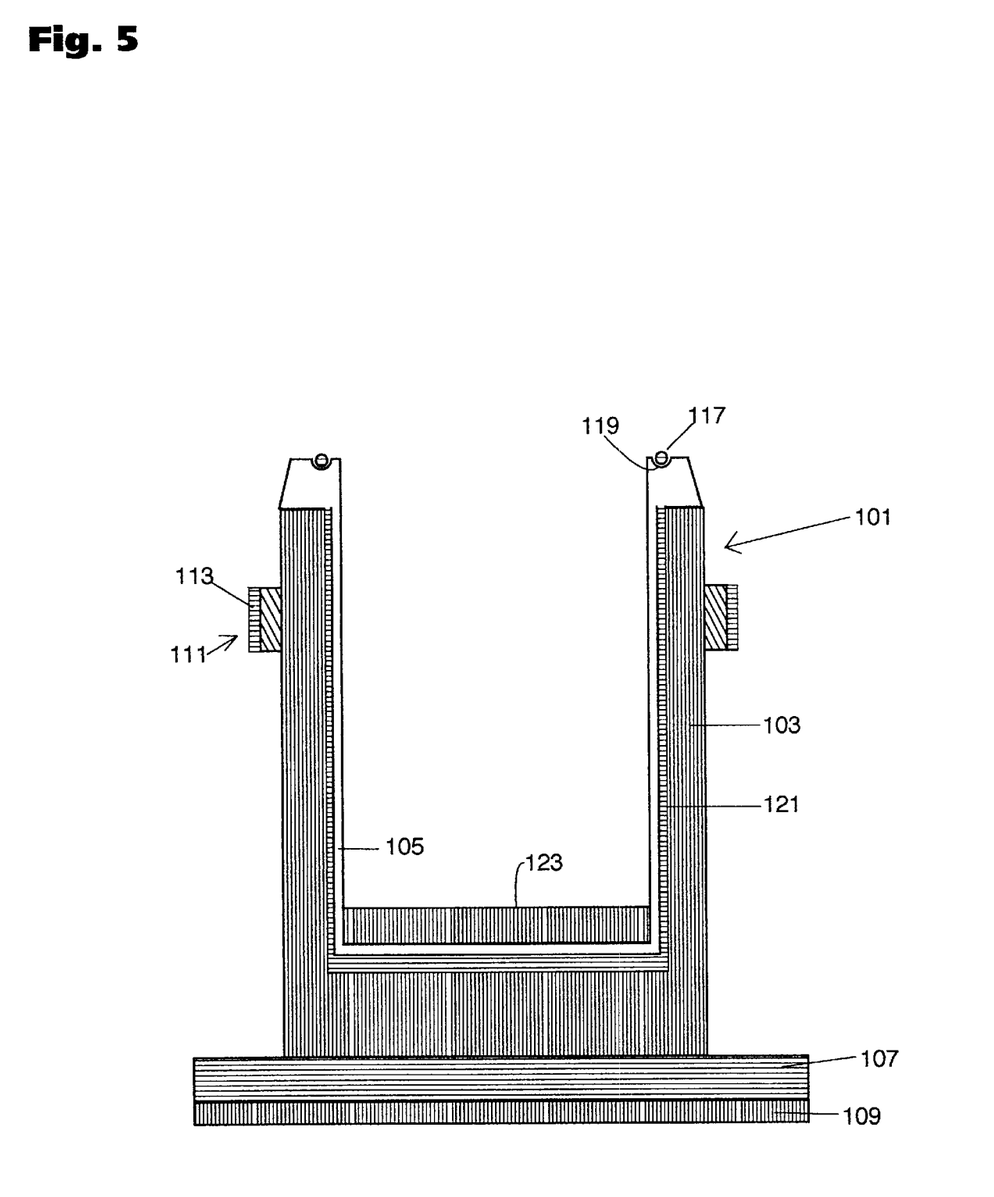
FIG. 5 is a sectional view of the container shield of FIG. 4, taken through section lines 5—5.

Turning now to FIGS. 4 and 5, a container shield 101 has a hollow cylindrical outer shell 103 that mates with an inner shell 105. A lead shield 121 is sandwiched between outer shell 103 and inner shell 105, and a resilient pad 123 lies at the bottom of inner shell 105. A rubber grommet 117 lies in a groove 119 at the top of inner shell 105. Outer shell 103 is connected to a base 107 which include a resilient sub-base 109. Four locking flanges 111 are evenly spaced around the outside of hollow cylindrical portion 103. Each locking flange 111 defines a locking detent 113. The underside 115 of each locking flange 111 is angled to be closer to base 107 near locking detent 113 and farther from base 107 away from locking detent 113.

Figure 7:
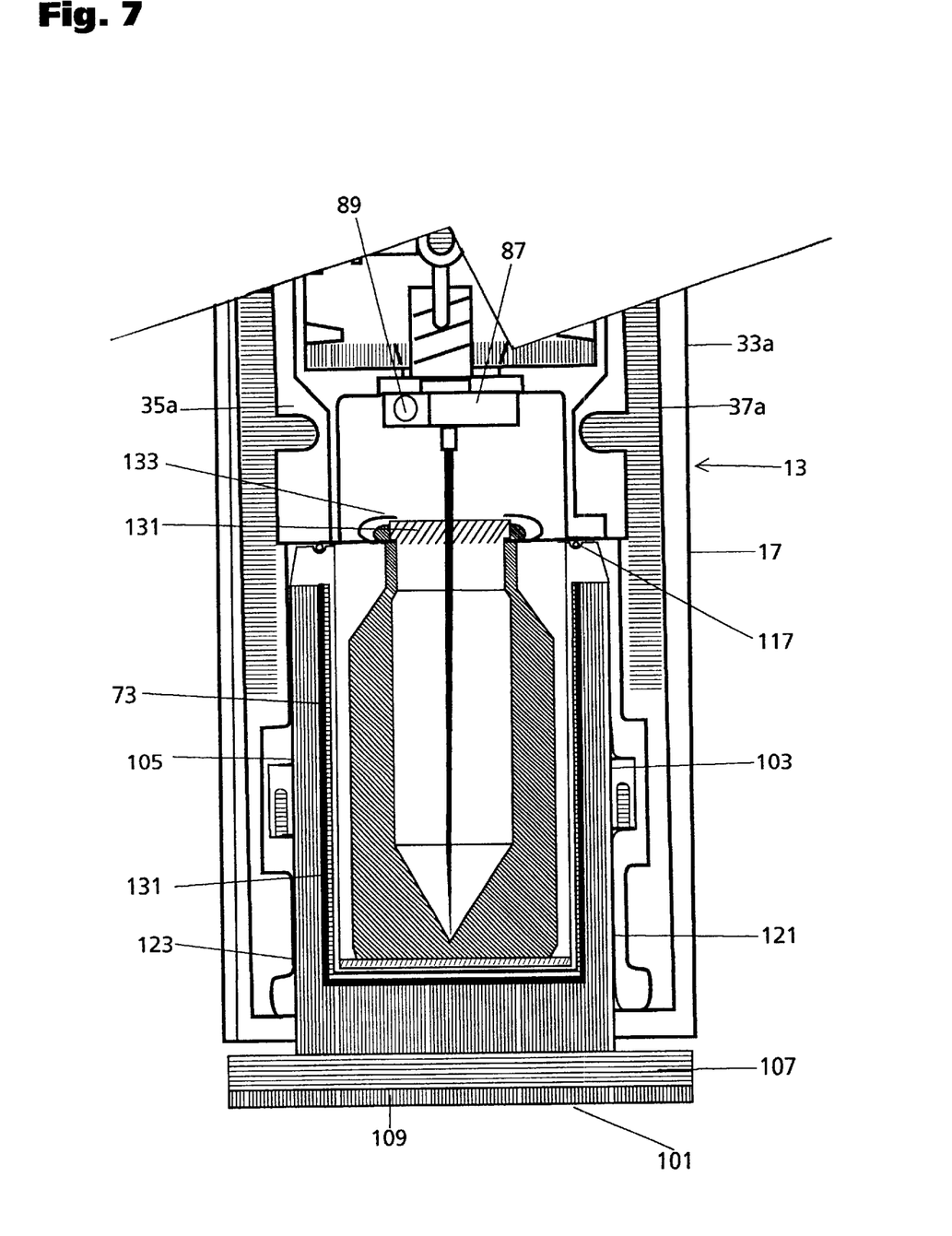
FIG. 7 is a sectional view of the lower portion of the manifold assembly of FIG. 1 with a container shield and container in place.

FIG. 7 shows container shield 101 in locking relationship with rear portion 17 of housing 13. To effect the locking relationship shown in FIG. 7, a glass vial 131 is inserted into container shield 101 where it rests on resilient pad 123. With container shield 101 sitting on a firm surface, housing 13 is lowered onto container shield 101, so that needle 73 punctures the rubber seal 133 which is held in place with metal cap 133 and grommet 117 will contact a portion of inner shell 35 and 35a, forming a liquid-tight seal. Housing 13 is then rotated about its longitudinal axis, so that pins 51 and 51a are pushed slightly downward by the underside 115 of locking flange 111, until they are directly under locking detent 113, where they move to lock container shield 101 to housing 13. When this locking relationship exists, the tip of needle 73 is at the bottom of vial 131 so as to be able to withdraw essentially all of the liquid in vial 131.

Pressure port 31 is connected to a means of providing fluid pressure (preferably a gas such as air) at pressures of about 0.1 to 0.4 MPa. Although a simple syringe could be used, preferred is a screw syringe of the type commonly used for angioplasty. A Model 2030 syringe made by ACS is an exemplary source of pressure. The pressure source also preferably includes a means for at least one of measuring the pressure, measuring the duration of a treatment, warning of a pressure exceeding a preset limit, or warning of a sudden los of pressure (which would indicate a leak in the system).

Outlet port 79 is connected to a radiation treatment balloon, which may be specially made for this application, or may be an ordinary balloon catheter of the type commonly used for angioplasty.

The manifold is designed such that it can be operated a number of different ways. However, the following method is believed to be optimal. To begin, pressure valve 65 is closed and fluid valve 67 is positioned to connect outlet path 71 and manifold tube 57.

Figure 6:
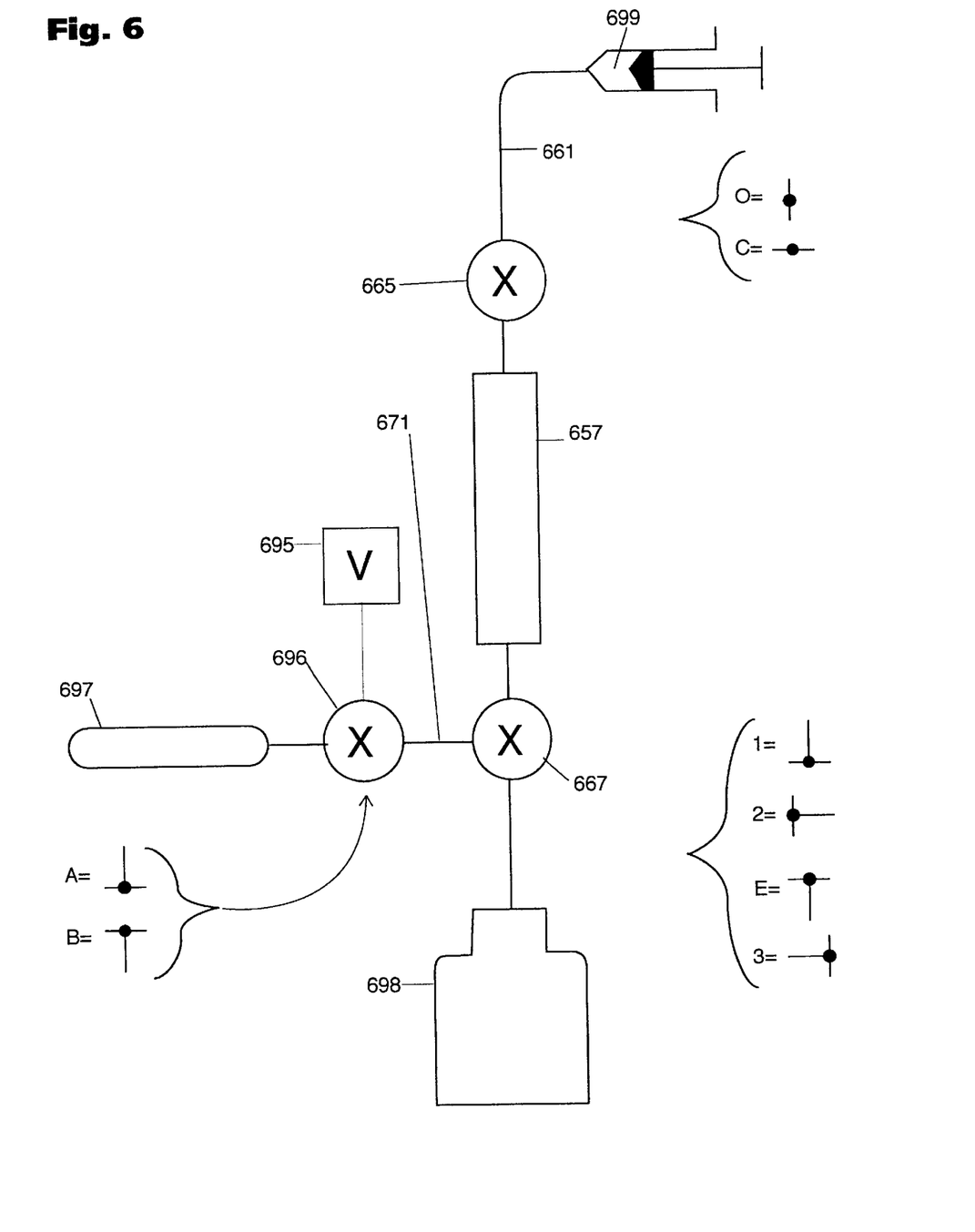
FIG. 6 is a schematic view of the a manifold assembly and associated components.

FIG. 6 shows a schematic representation of the manifold system of the invention. Manifold tube 657 is connected at one end to pressure path 661 via pressure valve 665 and at the other end to vial 698 and outlet port 679 via fluid valve 667. Outlet port 679 connects to the treatment balloon 697, passing through vacuum valve 696 which also connects to vacuum source 695. Adjacent to valves 665, 667, and 696 are schematic diagrams of the positions of the valves for various operating conditions.

EXAMPLE I

A human patient with a stenosed coronary artery was prepared for angioplasty by making an incision in the femoral artery. With the assistance of a fluoroscope, a guide wire was positioned past the stenosed region. A balloon catheter was fed onto the guide wire and advanced to the site of the stenosis. Diluted Hexabrix® X-ray contrast media (from Mallinckrodt Medical, Inc.) is forced out of an inflator syringe by hand to inflate the balloon to 1.5 MPa, opening the artery. The balloon was then deflated and the catheter withdrawn from the patient.

The radiation treatment procedure began with a device generally as described above, with vial 698 connected to fluid valve 667, pressure valve 665 in position C, fluid valve 667 in position 1, vacuum valve 696 in position A, and the manifold assembly 11 in an upright position. Treatment balloon 697 was inspected, tested, connected to the manifold assembly 11 via vacuum valve 696, and inserted into the patient.

Vacuum source 695 (a vacuum syringe) was activated and a vacuum drawn in treatment balloon 697 and manifold tube 657. Vacuum valve 696 was then turned to position B and the vacuum source 695 disconnected (the vacuum source will not be used further in a normal procedure, but may be used for emergency removal of radioactive fluid from the treatment balloon 697 in the event of failure of other components of the system).

Fluid valve 667 was then turned to position 2. The vacuum in the system caused the radioactive fluid in vial 698 to be drawn into manifold tube 657. After waiting a moment to ensure that all fluid movement has stopped, fluid valve 667 was then turned to position 3. This caused some of the radioactive fluid to move into treatment balloon 697. Fluid valve 667 was then turned to position 1, disconnecting the vial from the system.

Pressure source 699 (a screw-type syringe as described above) was attached to the system via pressure path 661 and pressure valve 665. Pressure valve 665 was then turned to position O. As pressure was applied by pressure source 699, treatment balloon 697 inflated, dosing the artery with radiation. Because the treatment blocked blood flow to the patient's heart, the treatment was interrupted to allow blood flow by reversing pressure source 699, deflating treatment balloon 697. After a few minutes, the treatment was resumed by again activating pressure source 699 to reinflate treatment balloon 697.

When the treatment was complete, pressure source 699 was again reversed and treatment balloon 697 deflated. Fluid valve 667 was turned to position 2 and pressure source 699 activated to force the radioactive fluid from manifold tube 657 into vial 698. To ensure complete removal of the radioactive fluid from treatment balloon 697, fluid valve 667 was turned to position 1, pressure source 699 was reversed, fluid valve 667 was turned to position 2, and pressure source 699 activated. Finally, fluid valve 667 was turned to position 1 and pressure valve 665 turned to position C. Treatment balloon 697 was then be withdrawn from the patient and the system disposed of in a manner consistent with the amount of radiation present.

EXAMPLE II (Hyptothetical)

The procedure of Example I was repeated, except that plug 59 in manifold tube 63 is porous rather than solid. By "porous" is meant that when dry, it will allow gasses to pass through it, but it will not allow liquids to pass through it. Thus, instead of using vacuum valve 696, vacuum source 695 is attached to pressure valve 665. Since plug 59 is porous, the air in the system passes through plug 59 to vacuum source 695.

As can be seen from the above, the manifold of the invention minimizes the amount of radioisotope needed for a procedure, and minimizes the hazards associated with manipulating a radioactive fluid.

What is claimed is:

1. A device for manipulating a radioactive fluid comprising:
   (a) a manifold for receiving a radioactive fluid;
   (b) an inlet path for introducing a radioactive fluid into the manifold;
   (c) an outlet path for expelling a radioactive fluid from the manifold;
   (d) a pressure path for introducing pressure into the manifold; and
   (e) a first valve means, connected to the manifold, the inlet path, and the outlet path, for controlling the communication of the manifold with the inlet path and the outlet path.

2. The device of claim 1, additionally comprising a second valve means, connected to the manifold and the pressure path, for controlling the communication of the manifold with the pressure path.

3. The device of claim 1, wherein the inlet path includes a hollow needle capable of puncturing a seal on a container containing a supply of radioactive fluid.

4. The device of claim 1, wherein the pressure path includes a pressure limiter to limit the maximum pressure in the manifold.

5. The device of claim 1, wherein the manifold has an interior generally in the shape of a cylinder; and wherein the device additionally comprises a plug within the manifold, the plug having a size and shape allowing it both to seal the manifold and to slide within the manifold under fluid pressure.

6. The device of claim 5, wherein the plug is impervious to liquids, but is penetrable by gasses.

7. The device of claim 5, wherein the plug is impervious to liquids and gasses.

8. The device of claim 1, additionally comprising a housing substantially surrounding the manifold, the housing including shielding to block radiation emitted from a radioactive fluid in the manifold.

9. The device of claim 8, wherein the inlet path includes a needle capable of puncturing a rubber seal on a bottle containing a supply of radioactive fluid; and the housing additionally surrounds at least a portion of the needle, and defines a passage leading toward the needle, so that if the needle is inserted into a container, the housing will also surround at lease a portion of the container.

10. The device of claim 9, additionally comprising a container shield, the container shield being shaped to receive a container containing a radioactive fluid, and being shaped to mate with the manifold.

11. The device of claim 10, wherein the container shield and the manifold are adapted to mate by motion which includes motion along the axis of the needle, so that when the container shield and the manifold are mated, the needle is capable of puncturing a seal on a container held in the container shield.

12. The device of claim 11, wherein the manifold and container shield are adapted to mate in a locking relationship.

13. A device for transferring a radioactive liquid from a container, comprising
   (a) a manifold having a first end and a second end, and having an interior the shape of a cylinder;
   (b) a plug within the manifold, the plug having generally the same cross section as the interior of the manifold, the plug sealing the manifold and being capable of sliding within the manifold under fluid pressure;
   (c) an inlet path for introducing a radioactive liquid into the manifold;
   (d) an outlet path for expelling a radioactive fluid from the manifold;
   (e) a pressure path for introducing a source of fluid pressure into the manifold;
   (f) a first valve connected to the first end of the manifold, the inlet path, and the outlet path, the first valve allowing the manifold to communicate with the outlet path, the manifold to communicate with the inlet path, the inlet path communicate with the outlet path, or the manifold to communicate with the inlet path and the outlet path; and
   (g) a second valve connected to the second end of the manifold, and the pressure path, allowing the manifold to communicate with the pressure path or block communication between the manifold and the pressure path.

14. The device of claim 13, additionally comprising a housing substantially surrounding the manifold and said first and second valves, the housing including shielding to block radiation from emitted from a radioactive liquid in the manifold; and additionally comprising first and second handles, extending through the housing, allowing the first and second valves to be manipulated from outside the housing.

15. The device of claim 14, wherein at least one of the first and second handles controls a corresponding valve by rotary motion, and includes a ratchet to allow the handle to be rotated in only one direction.

16. A method of transferring a radioactive fluid from a container comprising:
   (a) using a vacuum to draw a radioactive fluid from a container into a manifold that has fluid communication with the container through a first valve;
   (b) manipulating the first valve to interrupt the communication between the manifold and the container; and
   (c) using pressure to expel the radioactive fluid from the manifold to a location other than the container.

17. The method of claim 16, additionally comprising, after the step of using pressure to expel the radioactive fluid from the manifold to a location other than the container, of using a vacuum to withdraw the radioactive fluid from the location other than the container, back into the manifold.

18. The method of claim 17, additionally comprising, after the step of using a vacuum to withdraw the radioactive fluid from the location other than the container, back into the manifold, of using pressure to force the radioactive fluid back into the container.

19. A method of transferring a radioactive liquid from a container into a catheter, comprising:
   (a) applying a vacuum to a manifold;
   (b) providing a fluid connection between the manifold and a container containing a radioactive liquid, so as to withdraw the radioactive liquid from the container to the manifold;
   (c) interrupting, but not physically disconnecting, the fluid connection between the manifold and the container;
   (d) providing a fluid connection between the manifold and a catheter;
   (e) applying fluid pressure to the manifold to force the radioactive liquid from the manifold into the catheters.

20. The method of claim 19, additionally comprising the step of applying a vacuum to the manifold to withdraw the radioactive liquid from the catheter back into the manifold.

21. The method of claim 20, additionally comprising the step of interrupting the fluid connection between the manifold and the catheter.

22. The method of claim 21, additionally comprising the steps of reestablishing the fluid connection between the manifold and the container, and applying fluid pressure to the manifold to force the radioactive liquid back into the container.

23. A method of preventing restenosis in a human patient comprising:
   (a) inserting a balloon catheter into a patient to a site that has undergone or is about to undergo angioplasty;
   (b) providing a fluid connection between the balloon catheter and a manifold;
   (c) applying a vacuum to the manifold and the balloon catheter;
   (d) providing a fluid connection between the manifold and a container containing a radioactive liquid, so as to withdraw the radioactive liquid from the container to the manifold;
   (e) interrupting, but not physically disconnecting, the fluid connection between the manifold and the container;
   (f) applying fluid pressure to the manifold to force the radioactive liquid from the manifold into the balloon catheter, so as to inflate the balloon catheter with the radioactive liquid;
   (g) applying a vacuum to the manifold to withdraw the radioactive liquid from the balloon catheter back into the manifold.

24. The method of claim 23, wherein the fluid connection between the manifold and the container includes a hollow needle connected to the manifold, and the connection is made by moving the manifold and needle, along the axis of the needle, so that the needle pierces the container.

25. The method of claim 23, wherein the step of applying fluid pressure to the manifold includes a first sub-step of opening a valve that has been placed between the manifold and a source of fluid pressure.

26. The method of claim 23, wherein the fluid connection between the balloon catheter and the manifold is interrupted, but not physically disconnected, before the fluid connection between the manifold and the container is provided; and the fluid connection between the balloon catheter and the manifold is reestablished before the step of applying fluid pressure to the manifold to force the radioactive liquid from the manifold into the balloon catheter.

27. The method of claim 26, wherein the fluid connection between the balloon catheter and the manifold is reestablished before the step of interrupting, but not physically disconnecting, the fluid connection between the manifold and the container.

\* \* \* \* \*